United States Patent [19]
Grinstead

[11] 3,980,703
[45] Sept. 14, 1976

[54] EXTRACTION OF CARBOXYLIC ACIDS FROM DILUTE AQUEOUS SOLUTIONS

[75] Inventor: Robert R. Grinstead, Walnut Creek, Calif.

[73] Assignee: The Dow Chemical Company, Midland, Mich.

[22] Filed: Nov. 4, 1975

[21] Appl. No.: 628,616

Related U.S. Application Data

[62] Division of Ser. No. 467,328, May 6, 1974, which is a division of Ser. No. 285,546, Aug. 31, 1972, Pat. No. 3,816,524.

[52] U.S. Cl. .......................... 260/527 R; 260/465.4; 260/485 S; 260/526 N; 260/526 R; 260/535 R; 260/537 N; 260/537 R; 260/539 A; 260/539 R; 260/540; 260/541
[51] Int. Cl.² ............... C07C 51/48; C07C 121/407
[58] Field of Search ........ 260/527 R, 535 R, 537 R, 260/537 N, 539 R, 539 A, 465.4, 526 R, 526 N, 540, 541

[56] References Cited

UNITED STATES PATENTS

| | | | |
|---|---|---|---|
| 2,313,386 | 3/1943 | Levesque | 260/541 |
| 2,437,519 | 3/1948 | Guinot et al. | 260/465.4 |
| 2,480,380 | 8/1949 | Nicholl et al. | 260/465.4 |
| 2,574,256 | 11/1951 | Flisik et al. | 260/465.4 |
| 3,470,238 | 9/1969 | Asano et al. | 260/526 N |

Primary Examiner—Vivian Garner
Attorney, Agent, or Firm—J. Roger Lochhead

[57] ABSTRACT

Mono or dicarboxylic acids containing from two to four carbon atoms are extracted from dilute aqueous solutions with an organic liquid comprising one or more of the following extractants: dialkyl alkyl phosphonates, alkyl dialkyl phosphinates, trialkyl phosphine oxides, dialkyl alicyclic amidophosphates, dialkyl sulfoxides and tetralkyl ureas. An improved method for removing carboxylic acid contaminants from aqueous effluents or recycle streams is provided.

2 Claims, No Drawings

EXTRACTION OF CARBOXYLIC ACIDS FROM DILUTE AQUEOUS SOLUTIONS

CROSS-REFERENCE TO RELATED APPLICATION

This is a division of application Ser. No. 467,328, filed May 6, 1974 which in turn is a division application Ser. No. 285,546, filed Aug. 31, 1972, now U.S. Pat. No. 3,816,524.

BACKGROUND OF THE INVENTION

It has been proposed to recover various carboxylic acids from aqueous solutions by direct contact with several different types of polar organic extractants. For example, see the following patents:

| Patent | Acid Recovered | Extractant |
|---|---|---|
| U.S. 2,275,862 | Acetic | $C_6$–$C_{10}$ dialkyl ketones |
| U.S. 2,395,010 | Acetic | Aml Acetate or methyl amyl ketone |
| U.S. 2,446,231 | Acetic | Ethyl disulfide |
| U.S. 2,480,380 | Cyanoacetic | Methyl isobutyl ketone |
| Czech. 137,177 (C.A. 75: 63155y) | Formic, acetic or propionic | Cyclohexanone |

The organic extractants which have been proposed for recovery of carboxylic acids from aqueous solutions usually are not efficient enough for the processing of highly dilute solutions. In general, such solutions can be recycled or, if they do not also contain more toxic and/or persistent materials, can be discarded without constituting a serious source of pollution. However, this is not always the case. For example, the well-known process for making phenol from chlorobenzene produces a waste brine stream containing about 18–20 wt. % of sodium chloride, about 0.2% sodium acetate and trace amounts of phenol, benzene and acetone. Such streams, which cannot be disposed of in surface waters, also have too high a content of organics to be suitable as a feed to electrolytic chlor/alkali cells. It has now been found that such solutions can be made suitable as cell feeds at a minimal cost. The sodium acetate content of the brine stream is converted to sodium chloride and acetic acid by addition of an equivalent amount of hydrochloric acid. The acetic acid is then suitably removed by the practice of the instant invention.

SUMMARY OF THE INVENTION

Lower carboxylic acids are recovered from dilute aqueous solutions by contacting the solution with a liquid, water-immiscible organic solvent for the acid or acids. The aqueous solution comprises a total of two weight percent or less of one or more two to four carbon, mono- or dicarboxylic acids optionally substituted with from one to three chlorines or fluorines, or with one hydroxyl, oxo, cyano, methoxyl or ethoxyl group. The carbon to oxygen atomic ratio in each of said acids is not less than 1.0 nor greater than 2.0. The organic solvent comprises at least one weight percent of a polar extractant selected from the group consisting of:

a. dialkyl alkyl phosphonates,

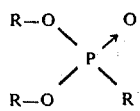

wherein each R is a $C_2$ to $C_{12}$ alkyl group, and the total number of carbons in the molecule is from 10 to 36;

b. alkyl dialkylphosphinates,

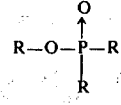

wherein each R is a $C_2$ to $C_{12}$ alkyl and the total number of carbons in the molecule is from 10 to 36;

c. trialkyl phosphine oxides,

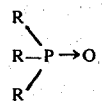

wherein each R is a $C_2$ to $C_{12}$ alkyl and the total number of carbons in the molecule is from 10 to 36;

d. dialkyl alicyclic amidophosphates

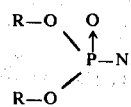

wherein each R is a $C_2$ to $C_{12}$ alkyl and R' is a $C_5$ to $C_7$ alicyclic radical, e. dialkyl sulfoxides,

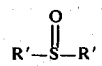

wherein each R' is a $C_3$ to $C_{12}$ alkyl group and the total number of carbons in the molecule is at least 8; and f. tetralkyl ureas,

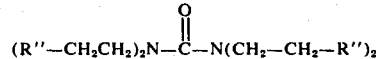

wherein each R'' is a $C_1$ to $C_7$ alkyl group and the total number of carbons in the molecule is from 12 to 36.

Representative lower carboxylic acids which may be recovered by the instant method are as follows:

| Acid | Formula | Atomic Ratio of Carbon to Oxygen |
|---|---|---|
| acetic | $CH_3COOH$ | 1.0 |
| propanoic | $C_2H_5COOH$ | 1.5 |
| butyric | $C_3H_7COOH$ | 2.0 |
| crotonic | $CH_3CH=CH-COOH$ | 2.0 |
| propiolic | $CH \equiv C-COOH$ | 1.5 |
| cyanoacetic | $HC-CH_2-COOH$ | 1.5 |
| lactic | $CH_3-CH(OH)COOH$ | 1.0 |
| glycolic; ethylether | $C_2H_5-O-CH_2-COOH$ | 1.33 |
| trifluoroacetic | $CF_3COOH$ | 1.0 |
| pyruvic | $CH_3-CO-COOH$ | 1.0 |
| lactic; methyl ether | $CH_3-CH(OCH_3)COOH$ | 1.33 |
| malonic; mono methyl ester | $CH_3-O-\overset{O}{\underset{\|}{C}}-CH_2-COOH$ | 1.0 |
| ethane-1,1-dicarboxylic | $HOOC-CH(CH_3)COOH$ | 1.0 |
| maleic or fumaric | $HOOC-CH=\lambda-CH-COOH$ | 1.0 |

-continued

| Acid | Formula | Atomic Ratio of Carbon to Oxygen |
| --- | --- | --- |
| 2,3-dichloroacrylic | Cl—CH=C—COOH<br>                \|<br>                Cl | 1.5 |
| acetylene dicarboxylic | HOOC—C≡C—COOH | 1.0 |
| methacrylic | $CH_2$=C($CH_3$)—COOH | 2.0 |

The aqueous solution of the acid or acids to be recovered may additionally comprise any other dissolved or suspended substances which do not interfere with the extraction of the acid into the organic phase. For example, other organic solutes, salts, suspended particles of carbon, ion-exchange resins or cellulosic fibers may be present. Whether or not other organics co-extract with the acid is immaterial to the instant invention. If co-extraction does occur and it is desired to separate the recovered acid, this can be done in a number of ways apparent to those skilled in the art. Since the primary utility of the present process is as a late stage cleanup step before disposal or recycle of an effluent, co-extraction of any other organics will generally be advantageous.

Suitable organic liquids for the practice of the present invention have a negligible solubility in the aqueous solution to be treated and comprise at least one weight percent of one or more polr extractants selected from groups (a) through (f) in the preceding list. These extractants have been found satisfactory for the removal of lower carboxylic acids from dilute aqueous solutions. Those extractants which are liquids at the contemplated temperature of operation can be employed neat or diluted with an organic solvent which has little or no solubility in the aqueous acid solution to be processed. Those extractants which are solids — such as trioctyl phosphine oxide — will necessarily be dissolved in such a solvent.

The concentration of the extractant in the organic phase is primarily viscosity limited, but may be as high as 100 percent.

Examples of suitable organic diluents are kerosene, carbon tetrachloride, amyl acetate, toluene, ethyl benzyl ketone, dibutyl ether, benzonitrile, 2,2-dichloro propane, heptane, 1-nitrobutane, triethyl phosphite, 1-pentanol, ethoxy(triethyl) silane and 1-fluoropentane.

The choice of a diluent will depend on several factors generally apparent to those skilled in the art. For example, the diluent must be a good enough solvent for the polar extractant or extractants to provide a total concentration of at least one weight percent. The diluent should not be significantly degraded by whatever physical or chemical treatment is used to strip the extracted acid from the loaded extractant solution. If stripping is done by contacting with an aqueous liquid, for example, the stripped extractant phase should be immiscible with an readily disengaged from the aqueous phase.

Any appropriate method may be used to remove the carboxylic acid from the loaded extractant or extractant solution. For example, the solution may be stripped simply by contacting it with water. Since the instant extractants have a pronounced affinity for lower carboxylic acids, a number of volumes of water will be required to affect stripping. However, unless other organics co-strip, the resultant dilute strip solution will present no serious disposal problem. A considerably more efficient method of stripping is to employ an aqueous solution of a base, such as sodium hydroxide. Alternatively, the loaded extractant phase may be directly contacted with gaseous ammonia and the resulting ammonium carboxylate separated by filtration or dissolved in a water wash. Still other methods will be apparent to those skilled in the art. In general, countercurrent stripping with an aqueous base is preferred.

SPECIFIC EMBODIMENTS

EXAMPLE 1

A solution of 1920 ppm (approximately 0.2 percent) of acetic acid in 18% aqueous NaCl was made up. A trace quantity of radioactive carbon-14 labeled acetic acid was included. Portions of this solution were shaken for thirty minutes with equal volumes of extractant solutions having the compositions set out in the following table. The phases were allowed to disengage, separated and their relative acetic acid concentrations determined by radiometric counting in a scintillation counter. The distribution coefficient (ratio of acetic acid concentrations in organic and aqueous phase) for each extraction is also given in the table.

| Polar Extractant | Concentration of Extractant | Solvent Used | Dist'n. Coeff. |
| --- | --- | --- | --- |
| Dibutyl butyl phosphonate | 0.1 M | Chevron 25* | 0.23 |
| Dibutyl butyl phosphonate | 0.5 | '' | 1.03 |
| Trioctyl phosphine oxide | 0.5 | '' | 6.1 |
| Diethyl cyclohexylamidophosphate | 0.5 | $CHCl_3$ | 1.13 |
| Di(n-butyl) sulfoxide | 0.1 | Chevron 25 | 0.18 |
| '' | 0.5 | '' | 1.00 |

*A high boiling mixture of alkylated aromatic hydrocarbons, 50% distillation point 161°C.

EXAMPLE 2.

In the manner of Example 1, about 0.025 molar aqueous solutions of acetic, glycolic and lactic acids were extracted with equal volumes of TOPO (trioctyl phosphine oxide) solutions in kerosene or Chevron 3. The distribution coefficients found are given in the following table.

| Solvent | TOPO Conc'n | Aqueous Phase | Distribution Coefficient For: | | |
| --- | --- | --- | --- | --- | --- |
| | | | Acetic | Glycolic | Lactic |
| Kerosene | 0.2 M | 1 Molar NaCl | 1.46 | 0.13 | 0.40 |
| Chevron 3* | 0.5 | '' | 3.2 | 0.39 | 1.4 |
| '' | '' | Water | 2.8 | 0.35 | 1.02 |

*A high boiling petroleum solvent consisting of a mixture of alkylated aromatic hydrocarbons, 50% distillation point—188°C.

It will be seen that glycolic acid (carbon to oxygen ratio of 2:3) is much less effectively extracted than acetic and lactic acids (carbon to oxygen ratios of 2:2 and 3:3, respectively).

EXAMPLE 3

Extraction of acids with tetra (n-butyl) urea

A 1.9% solution of acrylic acid in water was equilibrated with an equal volume of a 28% solution of tetra-(n-butyl) urea in cyclohexane. Titration of the separated phases revealed a distribution coefficient for the acrylic acid (organic/aqueous) of 1.05. A similar experiment with 0.2% acetic acid in 18% sodium chloride as the aqueous phase, and 0.5 M tetrabutyl urea in Chevron 25 as the extractant, gave a distribution coefficient of 0.40.

I claim:

1. A process for the recovery of lower carboxylic acids from dilute aqueous solution, comprising:
    contacting said aqueous solution with a water-immiscible, liquid organic solvent for said acid,
    said aqueous solution having a lower carboxylic acid content of two percent or less by weight, said content consisting of one or more two to four carbon mono- or dicarboxylic acids substituted with from zero to three chlorines or fluorines, or with zero or one hydroxyl, oxo, cyano, methoxyl or ethoxyl group, the carbon to oxygen atomic ratio in each of said acids being not less than 1.0 nor greater than 2.0,
    said organic solvent comprising a total of at least one weight percent of one or more polar extractants of the formula:

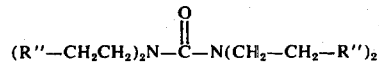

wherein each R'' is a $C_1$ to $C_7$ alkyl group and the total number of carbons in the molecule is from 12 to 36,
and separating the resulting loaded extractant and raffinate solutions.

2. The process of claim 1 in which said aqueous solution is a brine containing about 18–20 wt. percent of sodium chloride and about 0.2 wt. percent sodium acetate which has been treated with an amount of hydrochloric acid equivalent to the sodium acetate.

* * * * *